United States Patent [19]

Barak

[11] Patent Number: 5,728,134
[45] Date of Patent: Mar. 17, 1998

[54] METHOD AND APPARATUS FOR HEMOSTASIS

[76] Inventor: Shlomo Barak, 27 Smilanski Street, Rishon le Zion 75258, Israel

[21] Appl. No.: 715,160

[22] Filed: Sep. 17, 1996

[51] Int. Cl.$^6$ .................................................. A61B 17/00
[52] U.S. Cl. ........................... 606/214; 606/1; 128/899
[58] Field of Search .......................... 606/213, 215, 606/216, 214; 623/1, 11; 128/899; 604/93, 96, 181

[56] References Cited

U.S. PATENT DOCUMENTS

| 4,744,364 | 5/1988 | Kensey | 606/213 |
| 4,836,204 | 6/1989 | Landymore et al. | 606/215 |
| 5,217,024 | 6/1993 | Dorsey et al. | 128/758 |
| 5,413,571 | 5/1995 | Katsaros et al. | 606/213 |
| 5,419,765 | 5/1995 | Weldon et al. | 606/213 |
| 5,486,195 | 1/1996 | Myers et al. | 606/215 |

OTHER PUBLICATIONS

Compressar System, Instromedix Inc., 7431 NE Evergreen Parkway, Hillsboro, OR 97214–5898.
Perclose/Prostar Study—Micosoft Internet Explorer, Perclose Company, William Knopf, M.D. and Nicholas Lembo, M.D., Jun. 26, 1996, pp. 1–2.
Anglo–Seal, Haemostatic Puncture Closure Device, Sherwood Medical International, 1915 Olive Street, St. Louis, MO 63103–1642, 1995.

*Primary Examiner*—Jeffrey A. Schmidt
*Attorney, Agent, or Firm*—Abelman, Frayne & Schwab

[57] ABSTRACT

A method for hemostasis of an artery having a puncture after arterial catheterization, the catheterization using an introducer sheath, the method including the steps of inserting a catheter with a first balloon into the introducer sheath, positioning the first balloon against an outside surface of a wall of the artery at the puncture, inflating the first balloon against the outside surface of the artery at the puncture, and maintaining the first balloon against the puncture so that the first balloon substantially seals blood flow from the puncture so as to achieve hemostasis.

8 Claims, 13 Drawing Sheets

METHOD AND APPARATUS FOR HEMOSTASIS

FIELD OF THE INVENTION

The present invention relates to methods and apparatus for hemostasis following arterial catheterization.

BACKGROUND OF THE INVENTION

Catheterization is a well known medical procedure in which an instrument is introduced into an artery, such as the femoral artery. Removing the instrument introduced into the artery and stopping the flow of blood at the puncture site, i.e., causing hemostasis, poses a serious problem. For years the accepted method, still widely used today, is to apply constant manual pressure on the puncture site after removal of the catheter. However, this application of pressure is time consuming and painful to the patient, and since it depends largely on precise manual compression, may lead to fatigue of the surgeon, pose a risk of hematoma and aggravate the wound site. Furthermore, the limb of the patient with the puncture site must be kept motionless for hours.

Recently several devices have been introduced to attempt to solve the aforementioned problems. The COMPRESSAR system, commercially available from Istromedix, Inc. of Hilisboro, Oreg., is a type of clamp which applies mechanical pressure to the puncture site for hemostasis. A disadvantage of this compression device is that it is painful to the patient, and pressure must still be applied for about 20 minutes and the limb kept motionless for hours.

Another device is the ANGIO-SEAL hemostatic puncture closure device, commercially available from Sherwood Medical International, St. Louis, Mo. This device uses three absorbable components, consisting of an anchor, a collagen sponge and a suture. The anchor is positioned inside the artery and the collagen sponge is positioned outside the artery, both components being attached to the suture. The collagen sponge establishes the hemostasis and all components are absorbed in about three months in the body. However, the success of this system is not yet clear and adverse results have been reported.

Another device is called the PROSTAR Percutaneous Vascular Surgical Device, made by Perclose, Inc., U.S.A. This device is designed to deliver two polyester sutures to the puncture site and enable direct suturing of the artery.

SUMMARY OF THE INVENTION

The present invention seeks to provide improved apparatus and methods for establishing hemostasis following arterial catheterization. No external, painful mechanical or manual pressure is required and no foreign substances are left in the body.

The present invention uses a catheter equipped with a distal inflatable balloon. The catheter is inserted through an introducer sheath to the arterial puncture, until the balloon, still deflated, is inside the artery. The balloon is then inflated and the catheter withdrawn slightly until the inflated balloon reaches the arterial wall. This step establishes that the balloon is at the arterial wall. The balloon is then deflated and the catheter withdrawn an amount equal to the arterial wall thickness so that the balloon is now outside of the arterial wall. The balloon is then inflated once again and maintained in this position until hemostasis is attained, usually for about 20 minutes.

Other methods or apparatus may be used to accurately move the catheter across the arterial wall before re-inflating the balloon. Hemostatic agents may be introduced to the puncture site to further aid in hemostasis and no pressure is required. Although it may be advised to keep the patient's limb immobilized after completing the procedure, this is not an essential part of the procedure and is merely a precautionary measure to ensure that any clots and/or mended tissue formed at the arterial wall do not become loosened. Small movements of the limb are permitted. This is quite different from the prior art wherein complete immobilization of the limb is an essential part of the procedure.

There is thus provided in accordance with a preferred embodiment of the present invention, a method for hemostasis of an artery having a puncture after arterial catheterization, the catheterization using an introducer sheath, the method including the steps of inserting a catheter with a first balloon into the introducer sheath, positioning the first balloon against an outside surface of a wall of the artery at the puncture, inflating the first balloon against the outside surface of the artery at the puncture, and maintaining the first balloon against the puncture so that the first balloon substantially seals blood flow from the puncture so as to achieve hemostasis.

In accordance with a preferred embodiment of the present invention, the step of positioning includes the steps of inserting the catheter into the artery such that the first balloon is located inside the artery, inflating the first balloon, withdrawing the catheter until the first balloon is brought against an inner surface of the wall of the artery at the puncture, deflating the first balloon, withdrawing the catheter until the first balloon is located outside the artery at the puncture, and positioning the first balloon against an outside surface of a wall of the artery at the puncture.

Additionally in accordance with a preferred embodiment of the present invention, the step of positioning includes the steps of providing a second balloon mounted at a distal end of the catheter, the first balloon being proximal to the second balloon and spaced therefrom a distance approximately equal to a thickness of the wall of the artery, inserting the catheter into the artery such that the second balloon is positioned inside the artery and the first balloon is positioned outside the artery, inflating the second balloon, withdrawing the catheter until the second balloon is brought against an inner surface of the wall of the artery at the puncture, thereby positioning the first balloon against an outer surface of the wall of the artery, deflating the second balloon, and withdrawing the second balloon into the catheter.

Further in accordance with a preferred embodiment of the present invention, the step of positioning includes the steps of providing an anchor arranged for passage through a distal end of the catheter, the first balloon being proximal to the anchor, inserting the catheter into the artery such that the anchor is positioned inside the artery and the first balloon is positioned outside the artery, bringing the anchor against an inner surface of the wall of the artery at the puncture, thereby positioning the first balloon against an outer surface of the wall of the artery, and withdrawing the anchor into the catheter.

Still further in accordance with a preferred embodiment of the present invention, the method includes the step of introducing a hemostatic agent via the catheter to the puncture.

Additionally in accordance with a preferred embodiment of the present invention, the method further includes the step of observing the first balloon with fluoroscopy.

There is also provided in accordance with a preferred embodiment of the present invention, catheter apparatus including two depth indicators spaced from each other a distance approximately equal to a thickness of a wall of an artery.

The two depth indicators may comprise two inflatable balloons, or one inflatable balloon and one anchor, or two markings.

BRIEF DESCRIPTION OF THE DRAWINGS

The present invention will be understood and appreciated more fully from the following detailed description, taken in conjunction with the drawings in which:

FIGS. 1-7 are simplified, partially sectional, pictorial illustrations of a method and apparatus for hemostasis after arterial catheterization, in accordance with a preferred embodiment of the present invention, wherein:

FIGS. 8-12 are simplified, partially sectional, pictorial illustrations of a method and apparatus for hemostasis after arterial catheterization, in accordance with another preferred embodiment of the present invention, wherein:

FIGS. 13-16 are simplified, partially sectional, pictorial illustrations of a method and apparatus for hemostasis after arterial catheterization, in accordance with yet another preferred embodiment of the present invention, wherein:

DETAILED DESCRIPTION OF THE PREFERRED EMBODIMENTS

Reference is now made to FIGS. 1-7 which illustrate apparatus 10 for hemostasis after arterial catheterization, in accordance with a preferred embodiment of the present invention.

Figure 1:
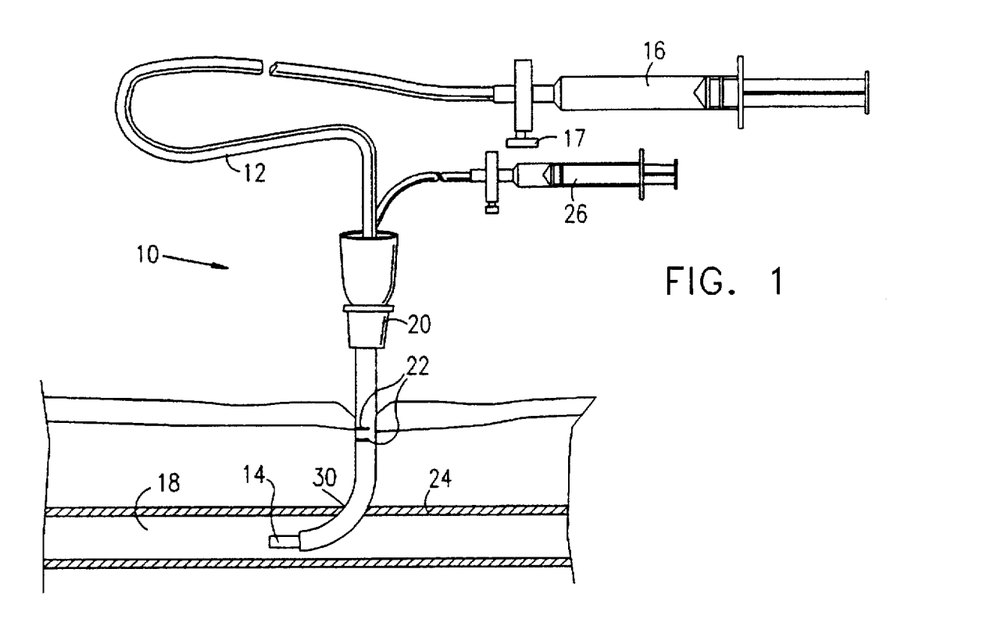
FIG. 1 illustrates inserting a catheter with a distal balloon into an artery via an introducer sheath.

Apparatus 10 preferably includes a catheter 12 with a distal balloon 14 in fluid communication with an inflation device such as a syringe 16 coupled with a stopcock 17. Balloon 14 is preferably inflated with air, although other fluids may be used. As seen in FIG. 1, catheter 12 is preferably introduced into an artery 18 via an introducer sheath 20. Introducer sheath 20 may be any conventional sheath, such as in the range of 6-11 F. Sheath 20 may be provided with a pair of depth indicators 22 spaced from each other a distance approximately equal to a thickness of a wall 24 of artery 18. Depth indicators 22 may comprise, for example, two markings printed or etched on sheath 20. Alternatively, depth indicators 22 may be located on catheter 12. An ancillary syringe 26 may be inserted in sheath 20 as well for introducing therein hemostatic agents or coagulants.

The operation of apparatus 10 and method for hemostasis in accordance with a preferred embodiment of the present invention are now described.

Figure 2:
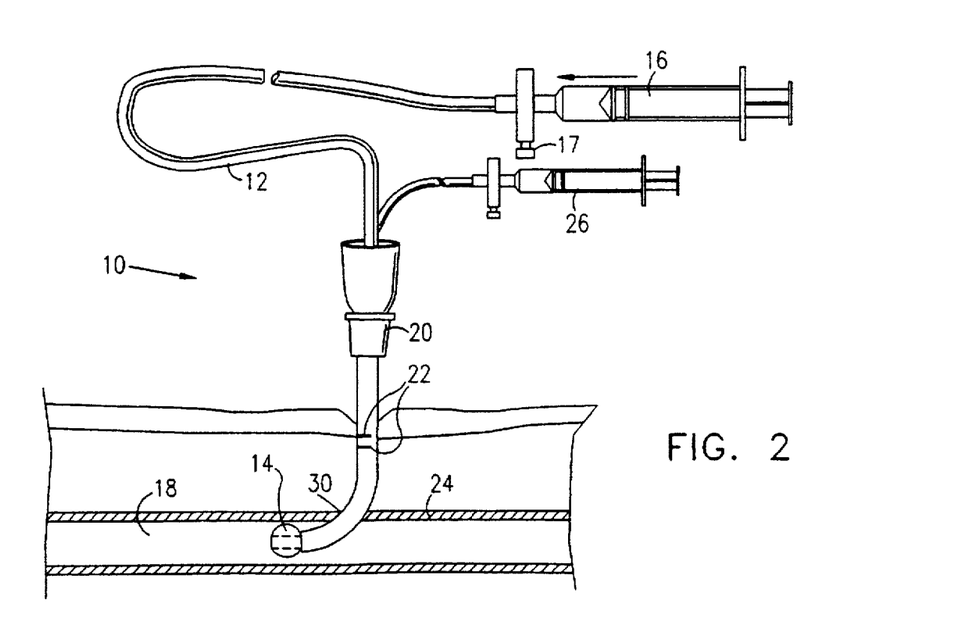
FIG. 2 illustrates inflating the balloon inside the artery.

In FIG. 1, balloon 14 is inside artery 18 and deflated. As seen in FIG. 2, syringe 16 may be used to inflate balloon 14 inside artery 18. Stopcock 17 is closed to keep balloon 14 inflated.

Figure 3:
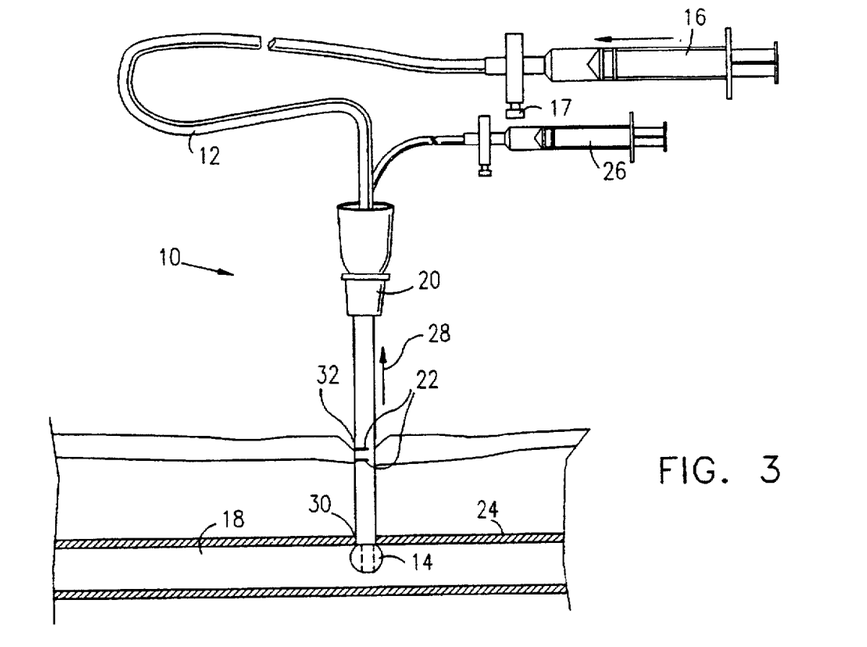
FIG. 3 illustrates withdrawing the catheter until the balloon is brought against the inner wall of the artery.
Figure 4:
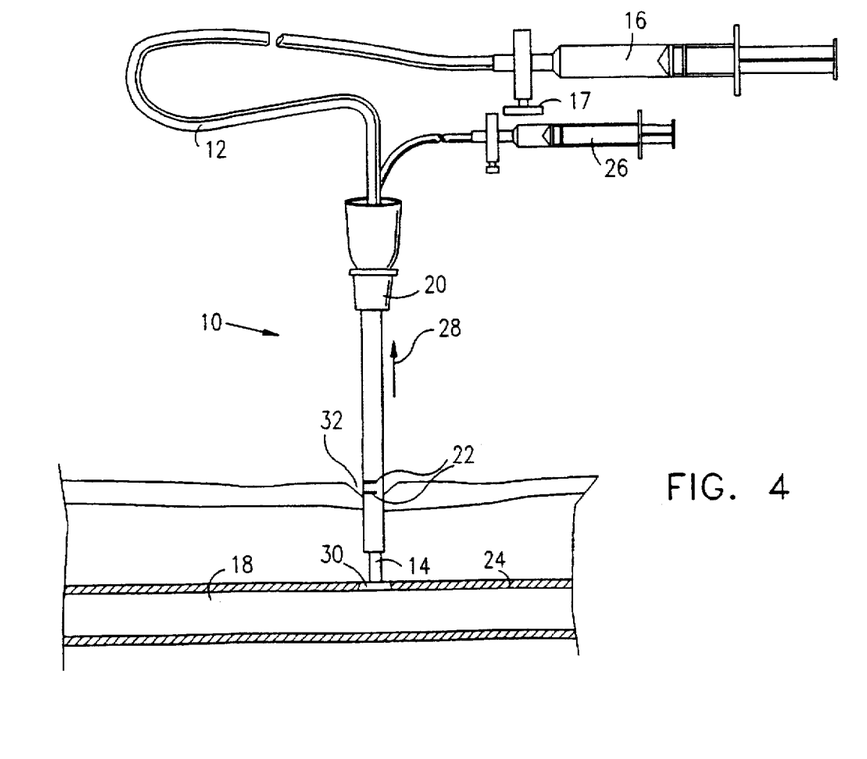
FIG. 4 illustrates deflating the balloon and further withdrawing the catheter outside of the artery.

In FIG. 3, catheter 12 is withdrawn generally in the direction of an arrow 28 until balloon 14 is brought against an inner surface of wall 24 of artery 18 at the site of a puncture 30. It is noted that the more proximal of the depth indicators 22 is substantially flush with a visible portion of skin 32. In FIG. 4, balloon 14 is then deflated by releasing stopcock 17, and catheter 12 is further withdrawn a distance approximately equal to the thickness of wall 24 generally in the direction of arrow 28 so that balloon 14 is positioned outside of artery 18. It is noted that the more distal of the depth indicators 22 is now substantially flush with visible portion of skin 32. At this stage of the procedure, blood may flow momentarily from puncture 30 but is still prevented from flowing out of the body by conventional seals and/or one-way valves located either in sheath 20 or other catheterization devices, as is known in the art. It is noted that a small flow of blood may be desirable to wash out blood clots.

Figure 5:
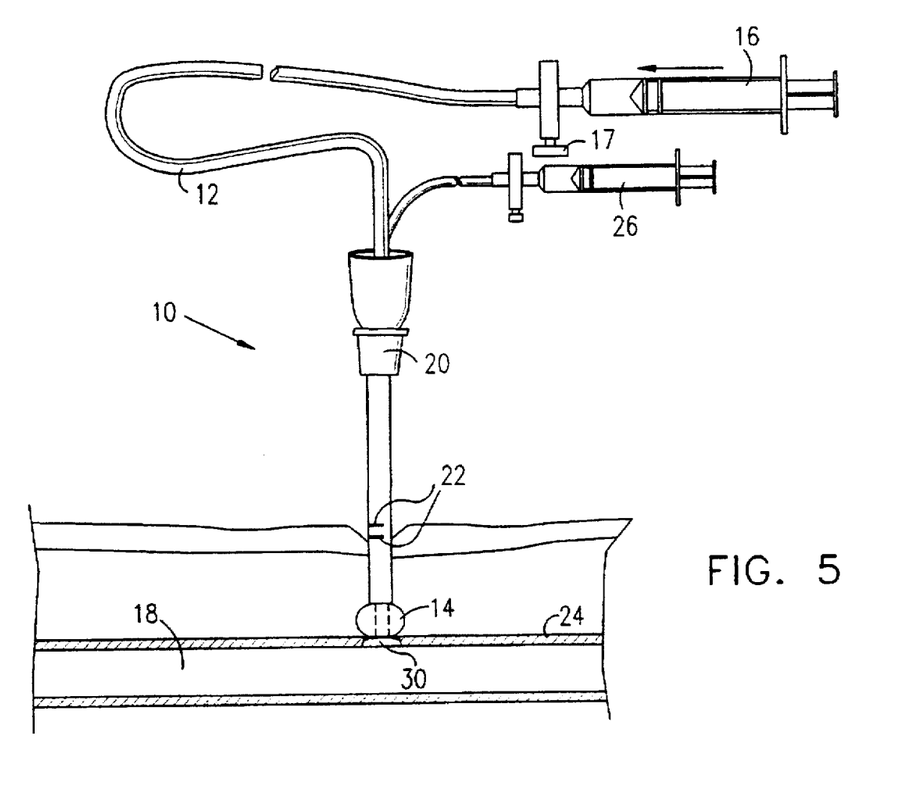
FIG. 5 illustrates inflating the balloon outside the artery.

In FIG. 5, stopcock 17 is opened and balloon 14 is re-inflated with syringe 16. Balloon 14 now substantially blocks flow of blood from puncture 30.

Figure 6:
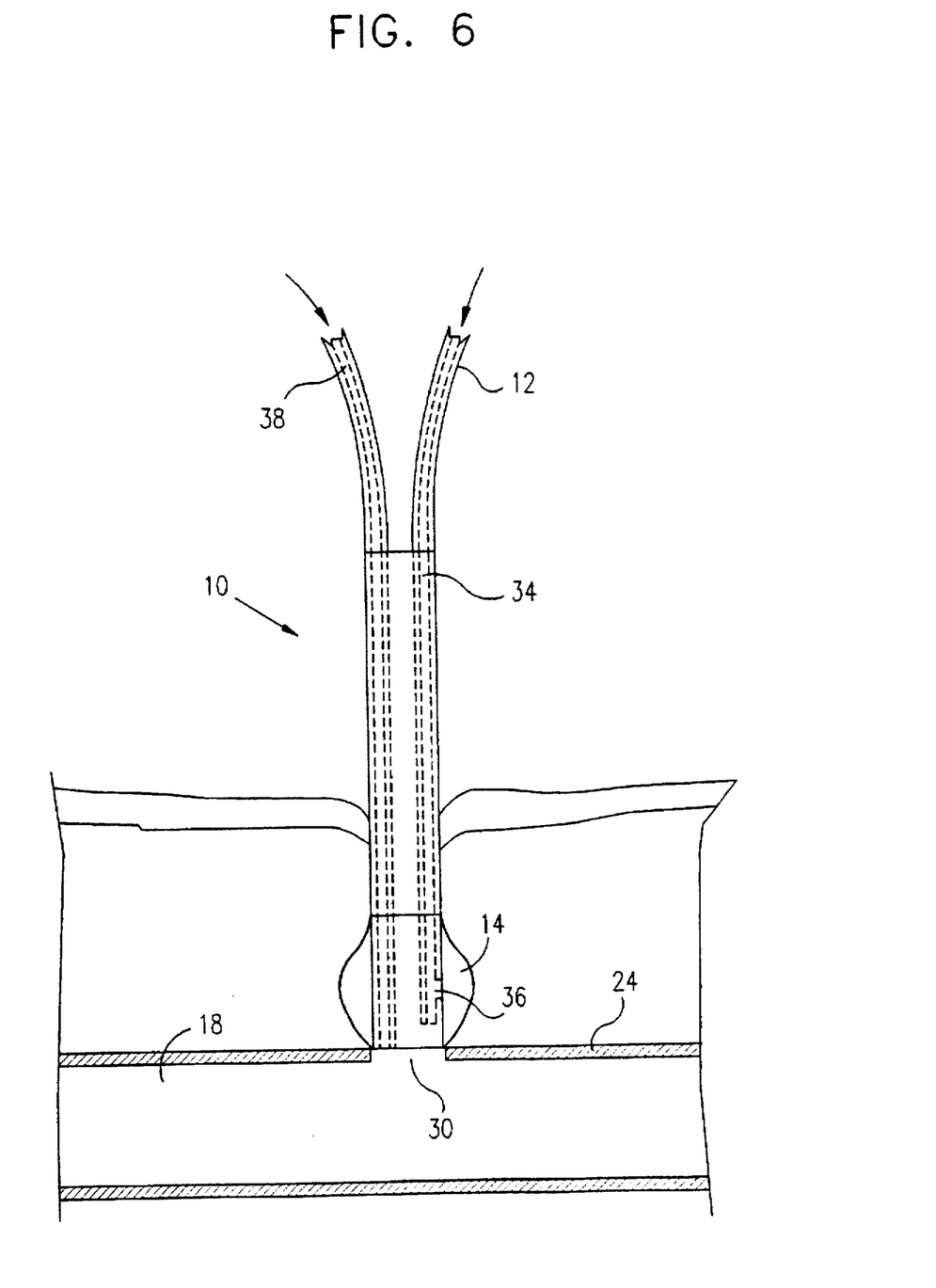
FIG. 6 is a more detailed illustration of the step illustrated in FIG. 5.

FIG. 6 is a more detailed illustration of the orientation of apparatus 10 shown in FIG. 5. In FIG. 6, it is seen that balloon 14 is sealingly positioned against puncture 30. Unlike the prior art, there is no need to exert manual or mechanical pressure on puncture 30. It is seen that catheter 12 preferably includes a lumen 34 which fluidly communicates with balloon 14 through an aperture 36. Air from syringe 16 (not shown in FIG. 6) is preferably passed through lumen 34 through aperture 36 to balloon 14 for inflation thereof. Another lumen 38 is preferably connected to syringe 26 (not shown in FIG. 6) for passing therethrough hemostatic agents.

Balloon 14 is maintained against puncture 30 until hemostasis is achieved. This usually takes about 20 minutes.

Figure 7:
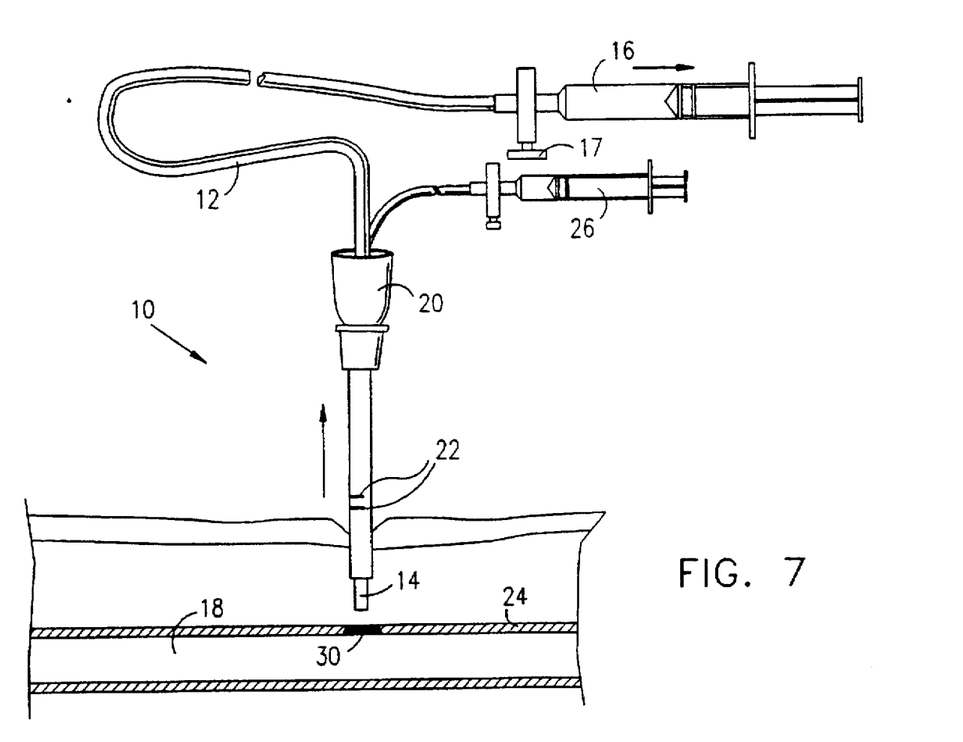
FIG. 7 illustrates achievement of hemostasis and removing the catheter from the body.

Referring to FIG. 7, it is seen that after achieving hemostasis in puncture 30, apparatus 10 may be removed from the body.

It is appreciated that the essential part of the above described procedure is sealingly positioning balloon 14 against puncture 30 to achieve hemostasis. The steps of inserting balloon 14 into artery 18, deflating balloon 14 and withdrawing the thickness of wall 24 are performed merely to ensure that balloon 14 is placed correctly against the outside of puncture 30. Fluoroscopy or other observation techniques may be used to observe the procedure and may even possibly be used to place balloon 14 correctly against the outside of puncture 30 without the need for inflation of balloon 14 inside artery 18 and subsequent deflation and withdrawal as described above.

Reference is now made to FIGS. 8–12 which illustrate apparatus 50 for hemostasis after arterial catheterization, in accordance with another preferred embodiment of the present invention.

Figure 8:
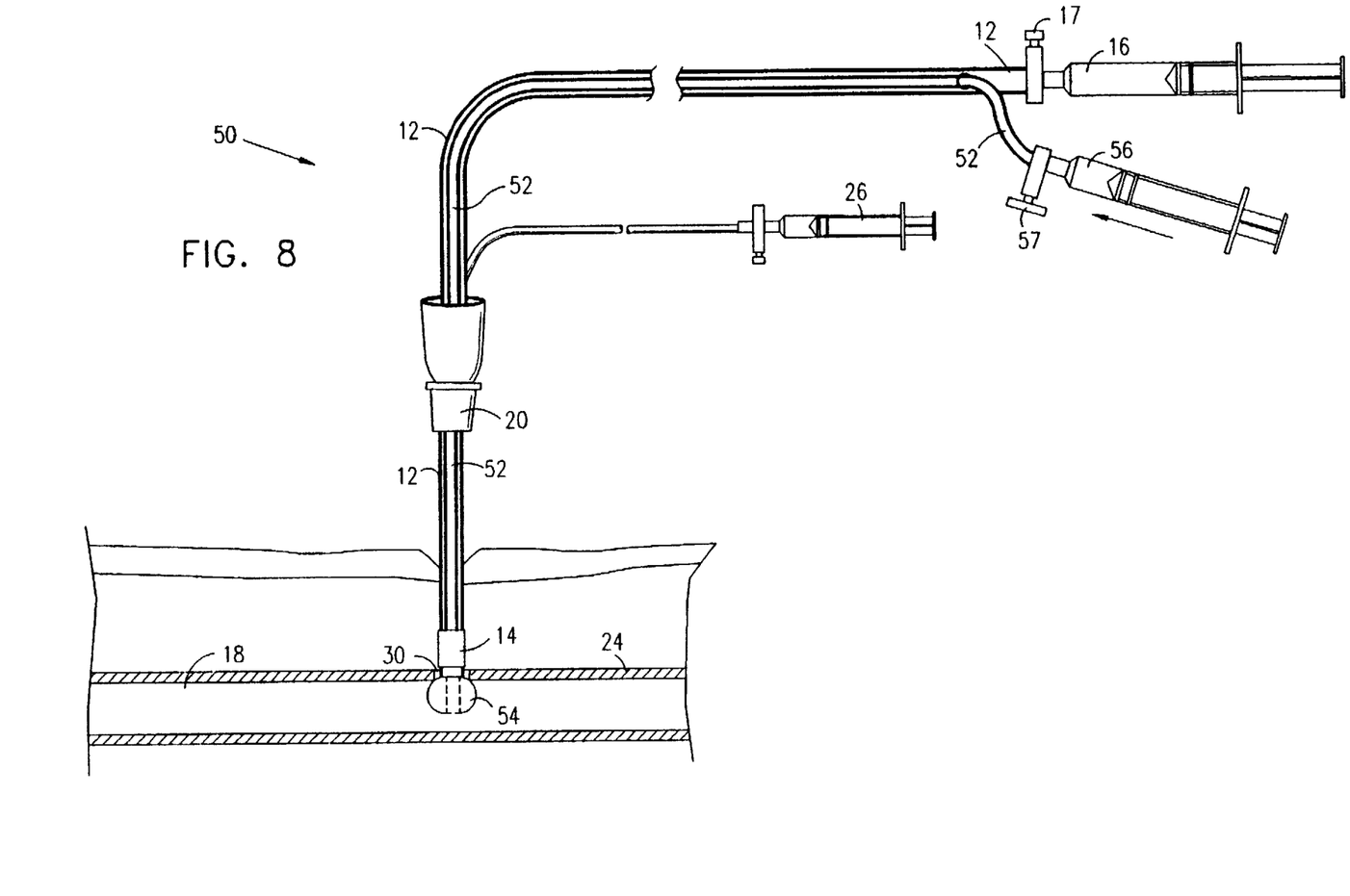
FIG. 8 illustrates inserting two balloon catheters, one inside the other, into an artery via an introducer sheath, the inner catheter having a distal balloon that serves as a guide and inner occluder, and the outer catheter having a proximal balloon that serves as an outer occluder.

Apparatus 50 is preferably similar to apparatus 10, with like elements being referenced by like numerals. As seen in FIG. 8, a second catheter 52 is disposed inside catheter 12. Catheter 52 preferably has a second balloon 54 mounted at a distal end thereof. Balloon 14 of catheter 12 is proximal to balloon 54 and spaced therefrom a distance approximately equal to the thickness of wall 24 of artery 18. A second inflation device, such as a syringe 56 coupled with a stopcock 57, is preferably in fluid communication with balloon 54.

In FIG. 8, catheters 12 and 52 are inserted into artery 18 such that balloon 54 is positioned inside artery 18 and balloon 14 is positioned outside artery 18. Balloon 54 thus serves as a guide for catheter 52. It is appreciated that a wire (not shown) could alternatively be used as a guide instead of balloon 54. Balloon 54 is then inflated while balloon 14 is deflated. Balloon 54 is brought against an inner surface of wall 24 of artery 18.

Figure 9:
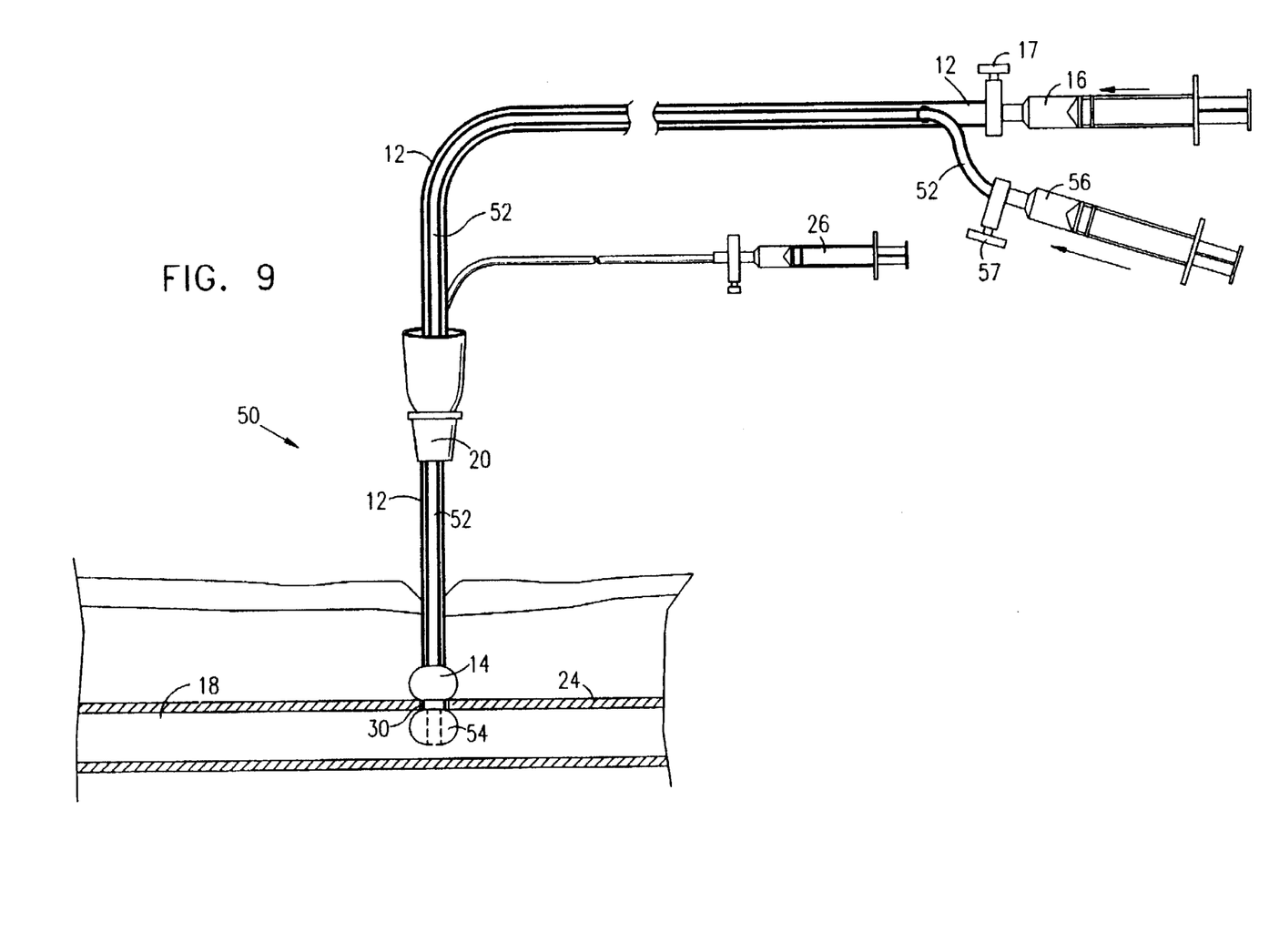
FIG. 9 illustrates inflating the proximal balloon outside the artery against the arterial wall.

In FIG. 9, balloon 14 is inflated, thereby "pinching" wall 24 of artery 18.

Figure 10:
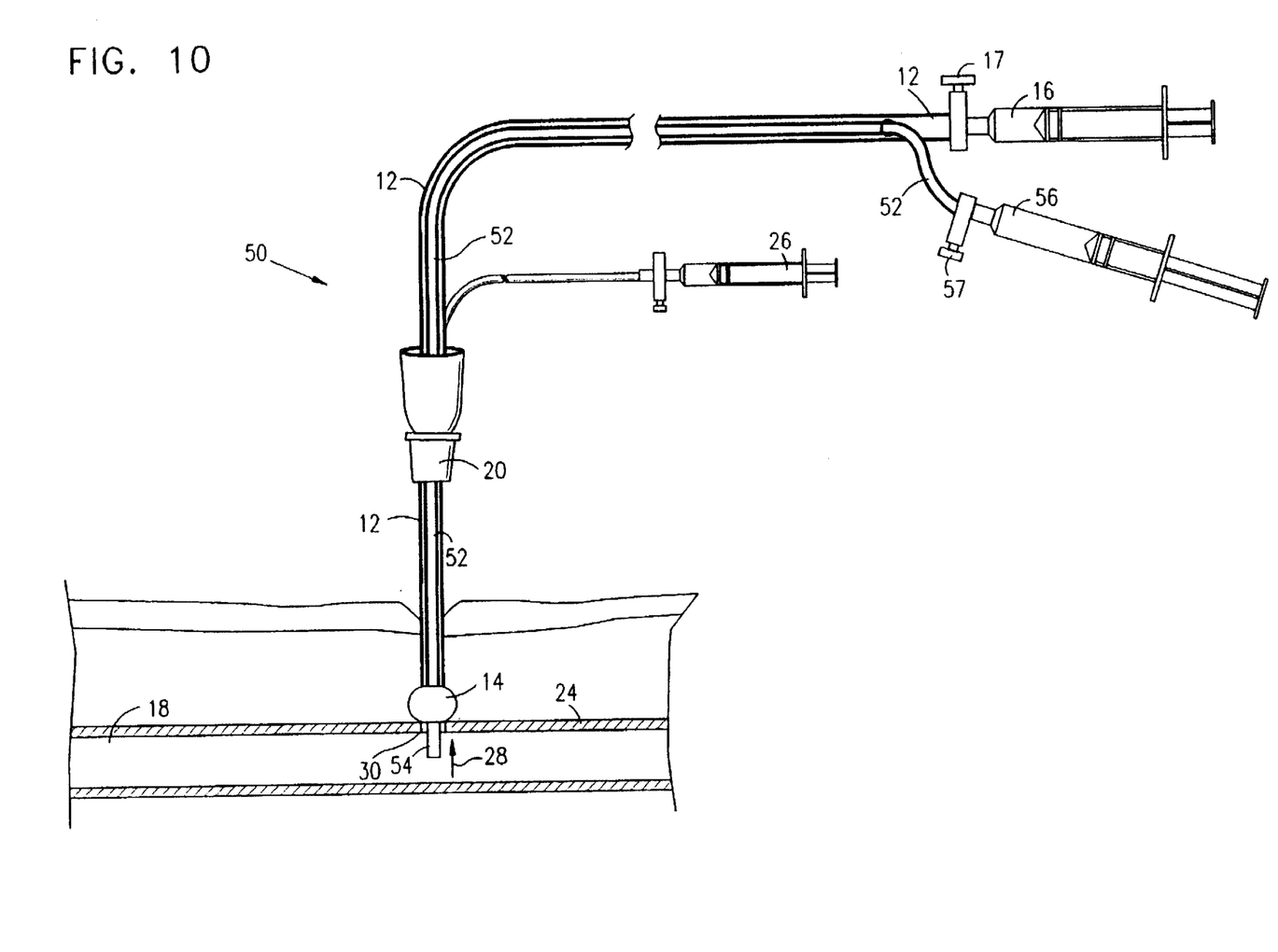
FIG. 10 illustrates deflating the distal balloon.
Figure 11:
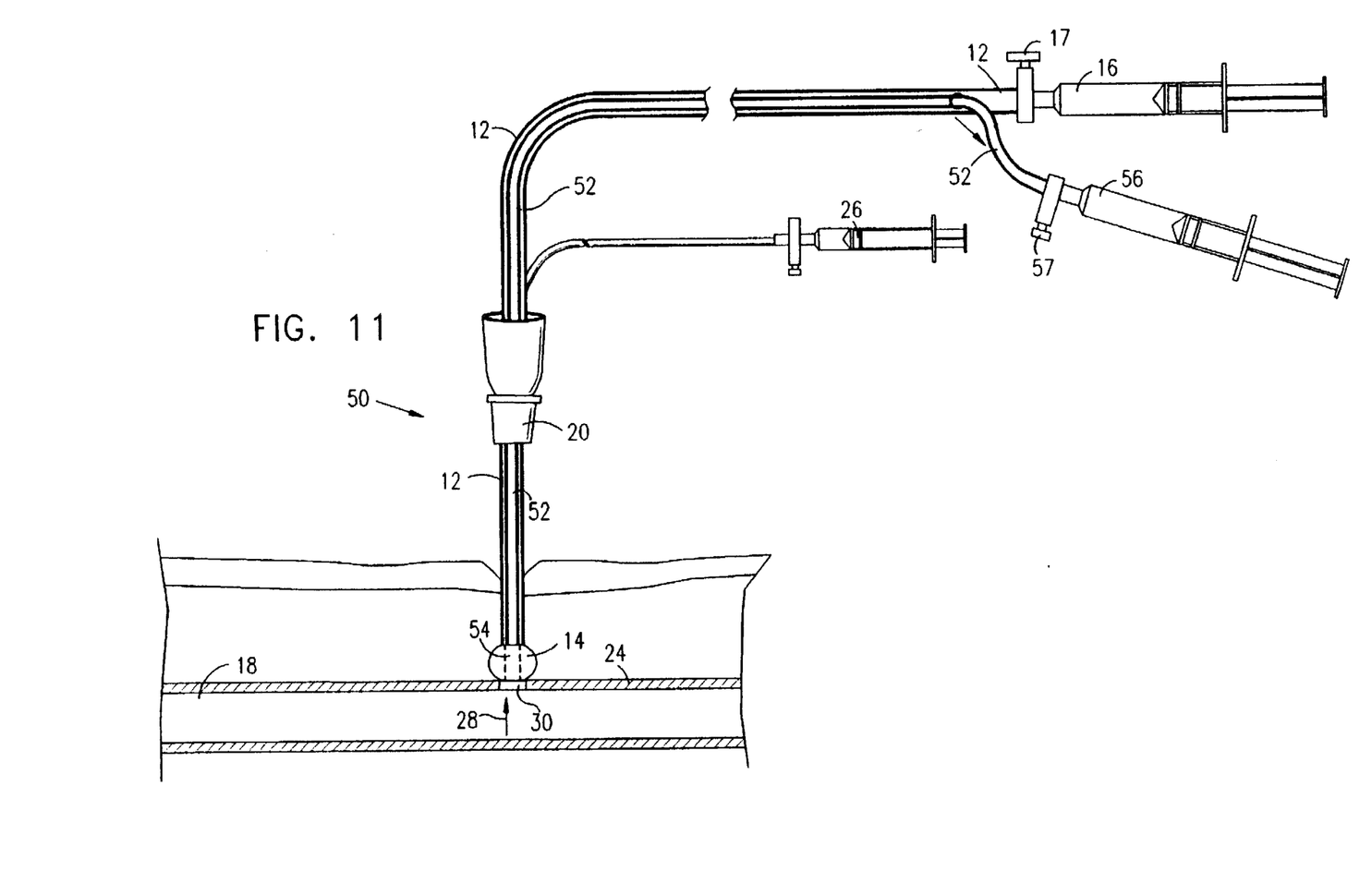
FIG. 11 illustrates withdrawing the distal deflated balloon outside of the artery, the proximal balloon being held against the outer arterial wall.

In FIG. 10 balloon 54 is deflated, and in FIG. 11 it is withdrawn generally in the direction of arrow 28 inwards into catheter 52. Inflated balloon 14 is maintained against puncture 30 until hemostasis is achieved.

Figure 12:
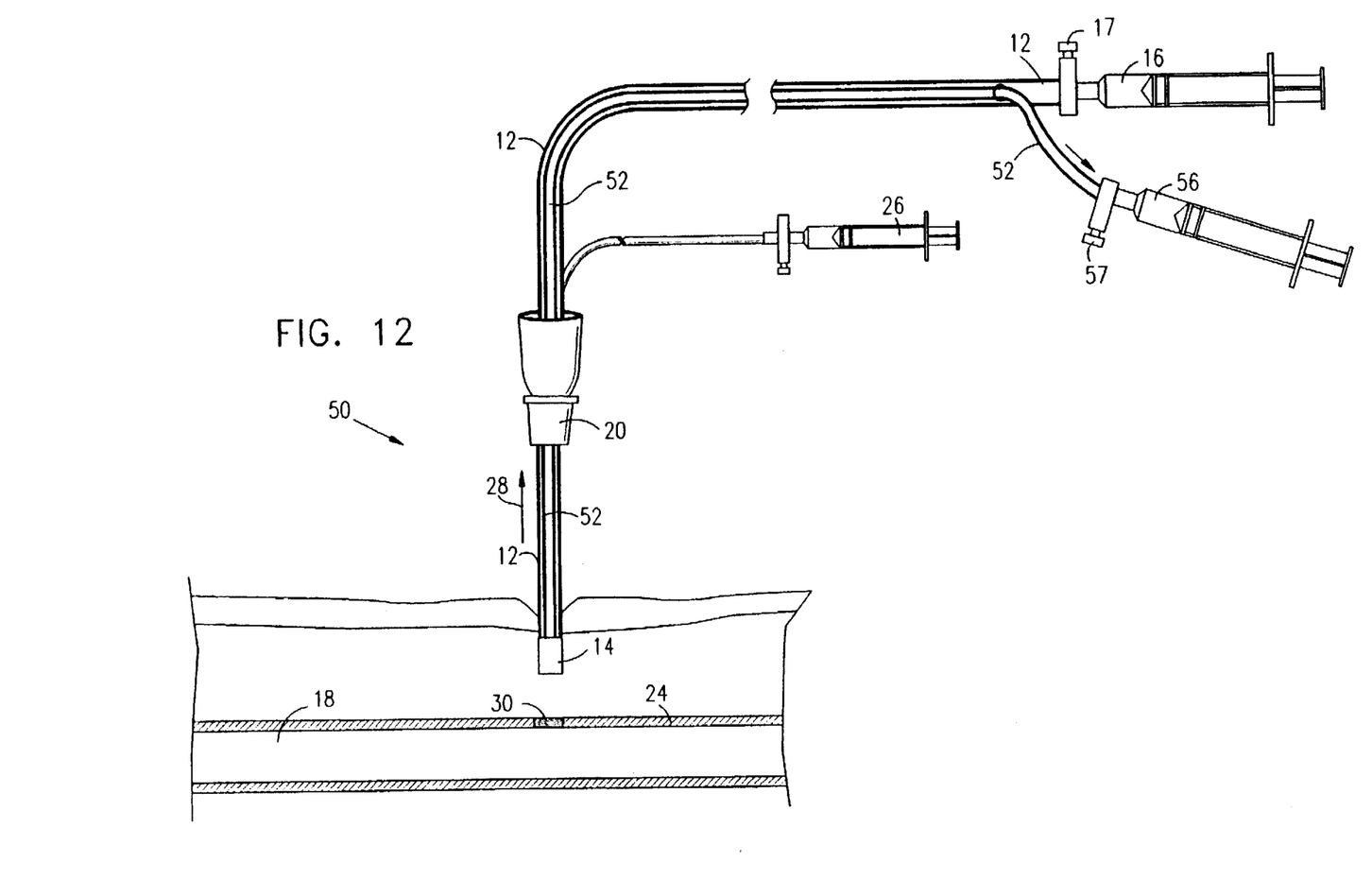
FIG. 12 illustrates achievement of hemostasis and removing the catheter from the body.

Referring to FIG. 12, it is seen that after achieving hemostasis in puncture 30, apparatus 50 may be removed from the body.

Reference is now made to FIGS. 13–16 which illustrate apparatus 70 for hemostasis after arterial catheterization, in accordance with yet another preferred embodiment of the present invention.

Apparatus 70 is preferably similar to apparatus 10, with like elements being referenced by like numerals. As seen particularly in FIG. 15, and as described hereinabove with respect to FIG. 6, catheter 12 preferably includes lumen 34 which communicates with balloon 14 via aperture 36. In addition, in apparatus 70, an anchor 72 is arranged for passage through catheter 12. Anchor 72 is preferably pivotally mounted at a distal end of a guide wire 74. A tilting wire 76 is preferably attached to a tip of anchor 72 for pivoting anchor 72 about a pivot 78.

Figure 13:
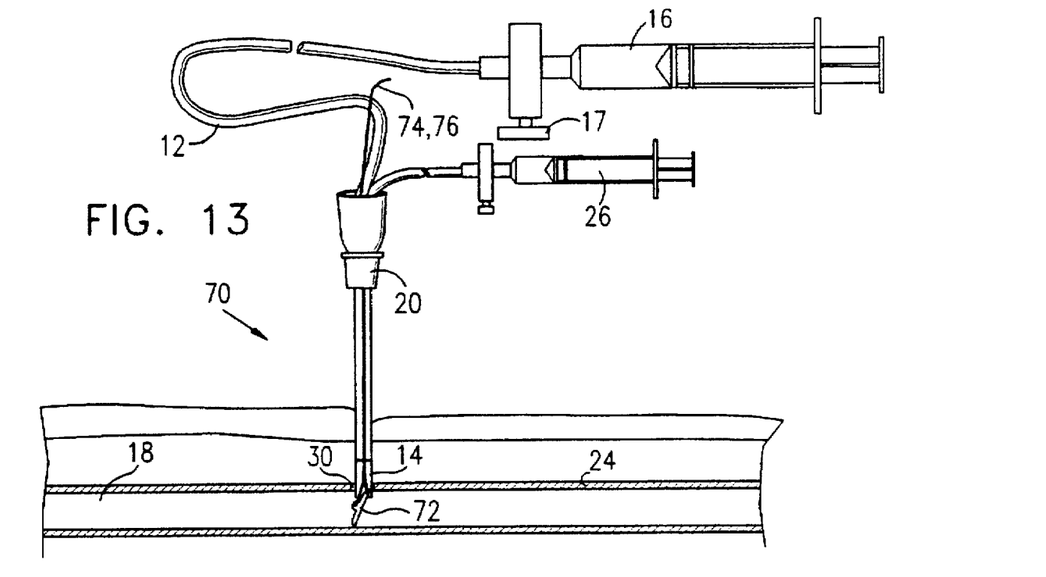
FIG. 13 illustrates inserting a catheter with a distal balloon and anchor into an artery via an introducer sheath.
Figure 14:
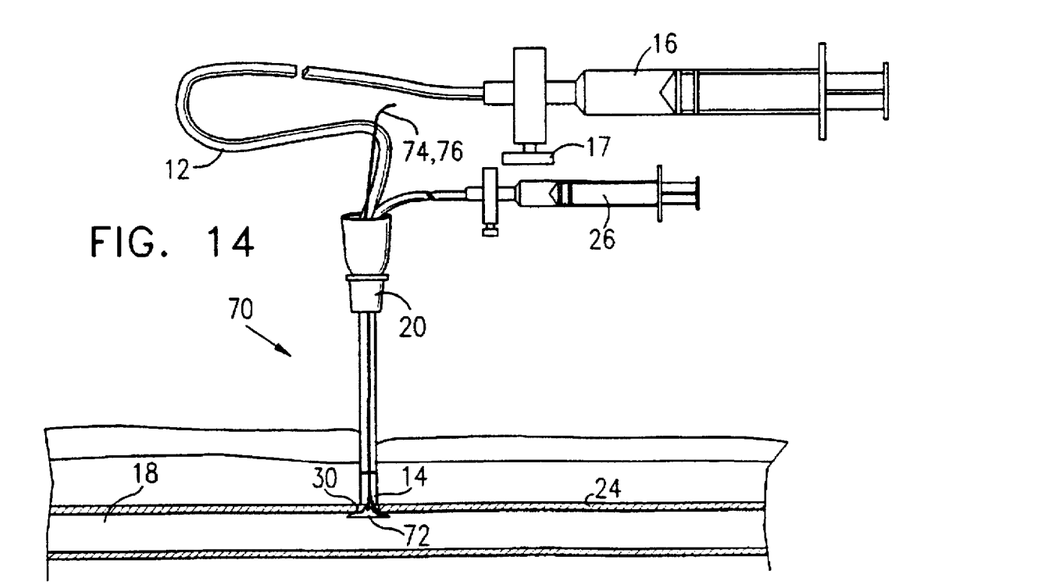
FIG. 14 illustrates withdrawing the anchor and bringing it against the inner wall of the artery.

Referring to FIG. 13, it is seen that catheter 12 is inserted into artery 18 such that anchor 72 is positioned inside artery 18 and deflated balloon 14 is positioned outside artery 18. In FIG. 14, anchor 72 is maneuvered and brought against an inner surface of wall 24 of artery 18.

Figure 15:
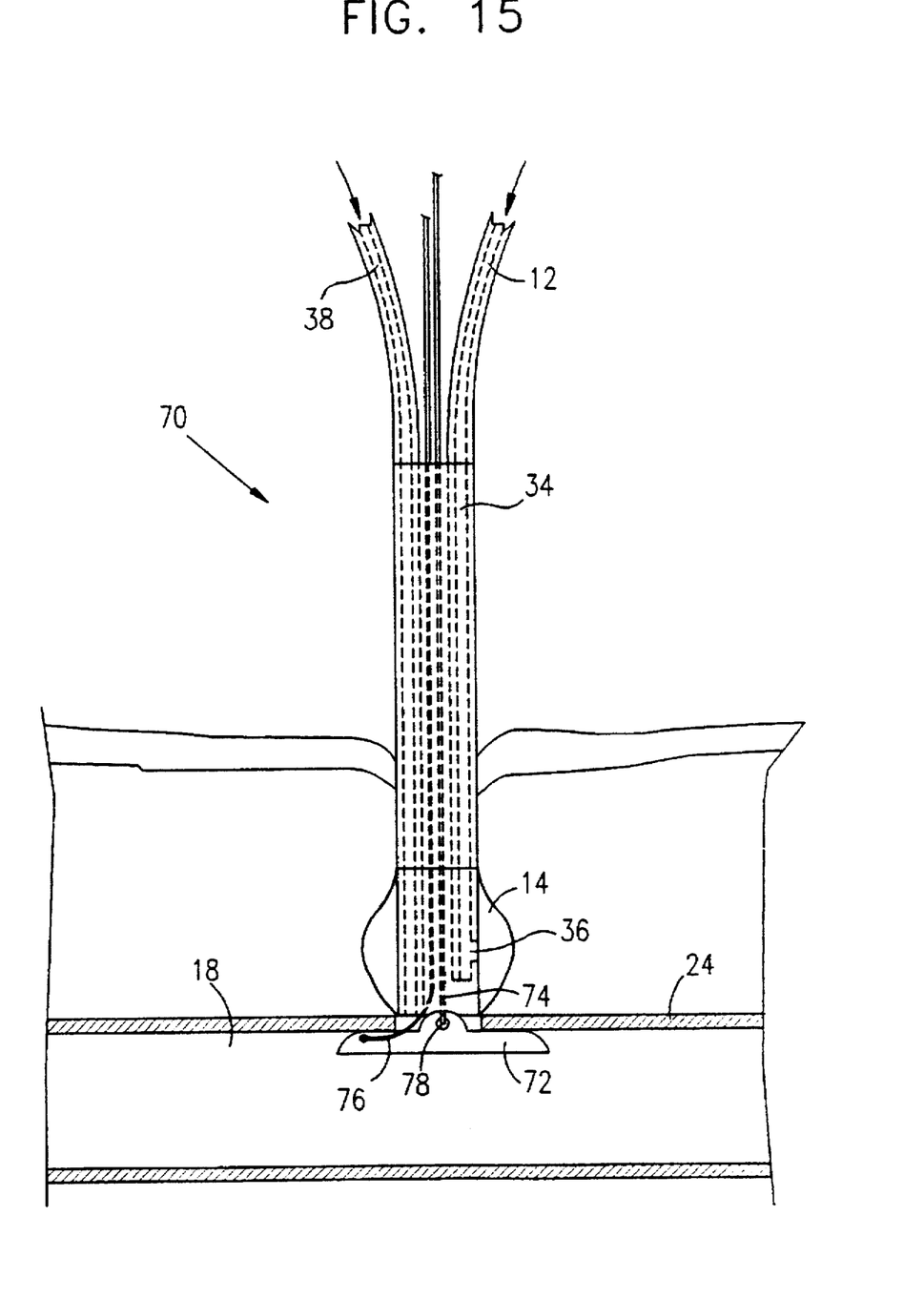
FIG. 15 illustrates inflating the balloon outside the artery and pushing the anchor distally away from the arterial wall.
Figure 16:
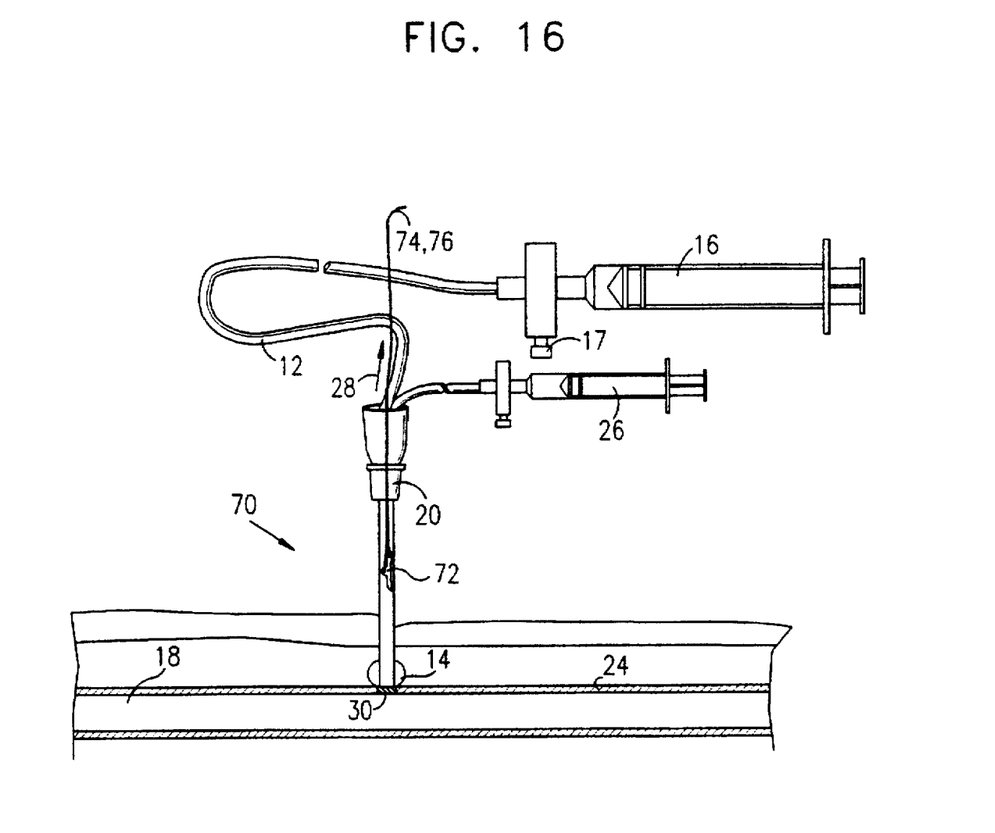
FIG. 16 illustrates achievement of hemostasis.

In FIG. 15, balloon 14 is inflated, thereby "pinching" wall 24 of artery 18.

in FIG. 16, anchor 72 is withdrawn generally in the direction of arrow 28 inwards into catheter 52. Inflated balloon 14 is maintained against puncture 30 until hemostasis is achieved.

It will be appreciated by persons skilled in the art that the present invention is not limited by what has been particularly shown and described hereinabove. Rather the scope of the present invention is defined only by the claims which follow:

What is claimed is:

1. A method for hemostasis of an artery having a puncture after arterial catheterization, said catheterization using an introducer sheath, the method comprising the steps of:
   inserting a catheter with a first balloon against an outside surface of a wall of said artery at said puncture;
   inflating said first balloon against said outside surface of said artery at said puncture; and
   maintaining said first balloon against said puncture so that said first balloon substantially seals blood flow from said puncture so as to achieve hemostasis,
   wherein said step of positioning comprises the steps of:
      inserting said catheter into said artery such that said first balloon is located inside said artery;
      inflating said first balloon;
      withdrawing said catheter until said first balloon is brought against an inner surface of said wall of said artery at said puncture;
      deflating said first balloon;
      withdrawing said catheter until said first balloon is located outside said artery at said puncture; and
      positioning said first balloon against an outside surface of a wall of said artery at said puncture.

2. The method according to claim 1 and further comprising the step of introducing a hemostatic agent via said catheter to said puncture.

3. The method according to claim 1 and further comprising the step of observing said first balloon with fluoroscopy.

4. A method for hemostasis of an artery having a puncture after arterial catheterization, said catheterization using an introducer sheath, the method comprising the steps of:
   inserting a first catheter with a first balloon against an outside surface of a wall of said artery at said puncture;
   inflating said first balloon against said outside surface of said artery at said puncture; and
   maintaining said first balloon against said puncture so that said first balloon substantially seals blood flow from said puncture so as to achieve hemostasis,
   wherein said step of positioning comprises the steps of:
      providing a second balloon mounted at a distal end of said first catheter and being connected to a second catheter disposed inside said first catheter, said first balloon being proximal to said second balloon and spaced therefrom a distance approximately equal to a thickness of said wall of said artery;
      inserting said first catheter into said artery such that said second balloon is positioned inside said artery and said first balloon is positioned outside said artery;
      inflating said second balloon;
      withdrawing said catheter until said second balloon is brought against an inner surface of said wall of said artery at said puncture, thereby positioning said first balloon against an outer surface of said wall of said artery;
      deflating said second balloon; and
      withdrawing said second balloon into said first catheter;
      and wherein said method also comprises following said maintaining step, the step of passing a hemostatic agent through said second catheter.

5. The method according to claim 4 and further comprising the step of observing said first balloon with fluoroscopy.

6. A method for hemostasis of an artery having a puncture after arterial catheterization, said catheterization using an introducer sheath, the method comprising the steps of:
   inserting a catheter with a first balloon against an outside surface of a wall of said artery at said puncture;

inflating said first balloon against said outside surface of said artery at said puncture; and maintaining said first balloon against said puncture so that said first balloon substantially seals blood flow from said puncture so as to achieve hemostasis, wherein said step of positioning comprises the steps of:
providing a non-inflatable anchor arranged for passage through a distal end of said catheter, said first balloon being proximal to said anchor;
inserting said catheter into said artery such that said anchor is positioned inside said artery and said first balloon is positioned outside said artery;
bringing said anchor against an inner surface of said wall of said artery at said puncture, thereby positioning said first balloon against an outer surface of said wall of said artery; and
withdrawing said anchor into said catheter.

7. Apparatus for hemostasis of an artery having a puncture after arterial catheterization, said apparatus comprising:
a first catheter having a first balloon arranged to be positioned against an outside surface of a wall of said artery at said puncture;
a first balloon inflator for inflating said first balloon against said outside surface of said artery at said puncture and maintaining said first balloon against said puncture so that said first balloon substantially seals blood flow from said puncture so as to achieve hemostasis,
a second catheter disposed inside of the first catheter and having a second balloon mounted at a distal end thereof, said first balloon being proximal to said second balloon and spaced therefrom a distance approximately equal to a thickness of said wall of said artery; and
an injector for supplying a hemostatic agent via said first catheter to the wall of said puncture following removal of said second catheter.

8. Apparatus for hemostasis of an artery having a puncture after arterial catheterization, said apparatus comprising:
a catheter having a first balloon arranged to be positioned against an outside surface of a wall of said artery at said puncture;
a first balloon inflator for inflating said first balloon against said outside surface of said artery at said puncture and maintaining said first balloon against said puncture so that said first balloon substantially seals blood flow from said puncture so as to achieve hemostasis; and
a non-inflatable anchor arranged for passage through a distal end of said catheter, said first balloon being proximal to said anchor.

* * * * *